US008198264B2

(12) United States Patent
Tahara et al.

(10) Patent No.: US 8,198,264 B2
(45) Date of Patent: Jun. 12, 2012

(54) METHOD FOR TREATING HEAD AND NECK CANCER

(75) Inventors: Makoto Tahara, Kashiwa (JP); Hironobu Minami, Kashiwa (JP)

(73) Assignee: National Cancer Center, Tokyo (JP)

( * ) Notice: Subject to any disclaimer, the term of this patent is extended or adjusted under 35 U.S.C. 154(b) by 957 days.

(21) Appl. No.: 11/412,792

(22) Filed: Apr. 28, 2006

(65) Prior Publication Data
US 2007/0254045 A1 Nov. 1, 2007

(51) Int. Cl.
*A61K 31/33* (2006.01)
(52) U.S. Cl. ...................................... 514/183
(58) Field of Classification Search .................. 514/183
See application file for complete search history.

(56) References Cited

U.S. PATENT DOCUMENTS 5,525,603 A 6/1996 Shirasaka et al.
6,767,531 B2 * 7/2004 Fritzberg et al. ............. 424/1.65

OTHER PUBLICATIONS

Takemura et al 'Phase I Clinical Study of a Concurrent Chemoradiotherapy using TS-1 and Nedaplatin' Japanese Journal of Cancer Chemotherapy, 32(13), p. 2065-2069, 2005.*
Takemura et al 'Phase I Clinical Study of a Concurrent Chemoradiotherapy using TS-1 and Nedaplatin' Japanese Journal of Cancer Chemotherapy, 32(13), p. 2065-2069, 2005. English Translation.*
Victor A. Marcial, M.D., et al., "Radiation Therapy Alone or in Combination With Surgery in Head and Neck Cancer", Cancer, vol. 55, No. 9, 1985, pp. 2259-2265.
David J. Adelstein, et al., "An Intergroup Phase III Comparison of Standard Radiation Therapy and Two Schedules of Concurrent Chemoradiotherapy in Patients With Unresectable Squamous Cell Head and Neck Cancer", J. Clinical Oncology, 21, 1, 2003, pp. 92-98.
David M. Brizel, M.D., et al., "Hyperfractionated Irradiation With or Without Concurrent Chemotherapy for Locally Advanced Head and Neck Cancer", The New England Journal of Medicine, vol. 338, No. 25, Jun. 18, 1998, pp. 1798-1804.
Marco Merlano, et al., "Reports", Journal of the National Cancer Institute, vol. 88, No. 9, May 1, 1996, pp. 583-589.
Branko Zakotnik, M.D., et al., "Concomitant Radiotherapy With Mitomycin C and Bleomycin Compared With Radiotherapy Alone in Inoperable Head and Neck Cancer: Final Report". Int J. Radiation Oncology Biol. Phys., vol. 41, No. 5, 1998, pp. 1121-1127.
David J. Adelstein, M.D., et al., "Mature Results of a Phase III Randomized Trial Comparing Concurrent Chemoradiotherapy with Radiation Therapy Alone in Patients with Stage III and IV Squamous Cell Carcinoma of the Head and Neck", Cancer, vol. 88, No. 4. Feb. 15, 2000, pp. 876-883.
Thomas G. Wendt, et al., "Simultaneous Radiochemotherapy Versus Radiotherapy Alone in Advanced Head and Neck Cancer: A Randomized Multicenter Study", Journal of Clinical, Oncol., vol. 16, No. 4, Apr. 1998, pp. 1318-1324.
J.P. Pignon, et al., "Chemotherapy added to locoregional treatment for head and neck squamous-cell carcinoma: three meta-analyses of updated individual data", The LANCET, vol. 355, Mar. 18, 2000, pp. 949-955.
George P. Browman, M.D., et al., "Choosing a Concomitant Chemotherapy and Radiotherapy Regimen for Squamous Cell Head and Neck Cancer: A Systematic Review of the Published Literature With Subgroup Analysis", Head & Neck, Clinical Review, Jul. 2001, pp. 579-589.
Julie Kish, et al., "Clinical Trial of Cisplatin and 5-FU Infusion as Initial Treatment for Advanced Squamous Cell Carcinoma of the Head and Neck", Cancer Treatment Reports, vol. 66, No. 3, Mar. 1982, pp. 471-474.
Jpn. J. Cancer Chemother, 28, 10, Oct. 2001, pp. 1381-1390 (with English Abstract).
Tsunehiro Takahashi, et al., "Histological Complete Response in a Case of Advanced Gastric Cancer Treated by Chemotherapy with S-1 Plus Low-dose Cisplatin and Radiation", Jpn. J. Clin. Oncol., 33, 11, 2003, pp. 584-588.
Hiroaki Iwase, et al., "Esophageal cancer with colonic metastasis successfully treated by chemoradiotherapy followed by chemotherapy with S-1 and cisplatin", Int. J. Clin. Oncol., 9, 2004, pp. 398-402.
Jpn. J. Cancer Chemother, 30, 12, Nov. 2003, pp. 1945-1947 (with English Abstract).
Jpn. J. Cancer Chemother, 30, 4, Apr. 2003, pp. 511-515 (with English Abstract).
Jpn. J. Cancer Chemother, 30, 9, Sep. 2003, pp. 1309-1312 (with English Abstract).
Jpn. J. Cancer Chemother, 31, 2, Feb. 2004 pp. 215-217 (with English Abstract).
Sotaro Kamei, et al., "NAC using CDDP+TS-1 in combination-Phase I Study in head and neck cancer", Head and Neck Cancer, vol. 30, No. 2, 2004, p. 282, (with Full English Translation).
Koji Harada, et al., "Combined effects of the oral fluoropyrimidine anticancer agent, S-1 and radiation on human oral cancer cells", Oral Oncology, 40, 2004, pp. 713-719.
M. Fujii, et al., "A phase I/II study of S-1 plus cisplatin (CDDP) in patients with head and neck cancer (HNC)", Journal of Clinical Oncology, 2005 ASCO Annual Meeting Proceedings, vol. 23, No. 16S, 5552, 2005, 2 pages (English Abstract Only).
M. Tahara, et al., "Phase I study of concurrent chemoradiotherapy (CRT) with S-1 and cisplatin (CDDP) in patients (pts) with unresectable locally advanced squamous cell carcinoma of head and neck (SCCHN)", Journal of Clinical Oncology, 2005 ASCO Annual Meeting Proceedings, vol. 23, No. 16S, 5575, 2005, 2 pages (English Abstract Only).
Villar, et al., "Cisplatin alone or in combination with adriamycin in the treatment of patients with head and neck cancer relapsed after radiotheraphy and/or surgery", Rev. Esp. Oncol., vol. 28(3), pp. 395-412, 1981. (English abstract only).
Okamoto, et al., "The usefulness of TS-1 for the treatment of head and neck cancer", Gan to Kagaku Ryoho, vol. 30(8), pp. 1119-24, Aug. 2003. (English abstract only).

* cited by examiner

*Primary Examiner* — Brandon Fetterolf
*Assistant Examiner* — Christopher R Stone
(74) *Attorney, Agent, or Firm* — Oblon, Spivak, McClelland, Maier & Neustadt, L.L.P.

(57) ABSTRACT

The present invention is directed to a method for the treatment of advanced head and neck cancer, the method including administering, in combination, S-1 and cisplatin and concurrently performing radiation.

23 Claims, 4 Drawing Sheets

| | | |
|---|---|---|
| Sex | Female | 1 |
| | Male | 16 |
| Age (years) | median | 62 |
| | range | 45-73 |
| PS | 0 | 12 |
| | 1 | 5 |
| Primary site | Hypopharynx | 9 |
| | Pharynx | 1 |
| | Oropharynx | 6 |
| | Nasopharynx | 1 |

| | T1 | T2 | T3 | T4 | LR | Total |
|---|---|---|---|---|---|---|
| N0 | - | - | - | 1 | 1 | 2 |
| N1 | - | - | - | - | - | 0 |
| N2 | - | - | 1 | - | - | 1 |
| N2a | - | - | - | 1 | - | 1 |
| N2b | 1 | - | - | - | - | 1 |
| N2c | 1 | 2 | 1 | 2 | - | 6 |
| N3 | 1 | 2 | - | 3 | - | 6 |
| Total | 3 | 4 | 2 | 7 | 1 | |

LR: local relapse

| Toxicity | Dose level 1 (S-1 40 mg/m²) N=3 | | Dose level 2 (S-1 60mg/m²) N=7 | | Dose level 3 (S-1 80mg/m²) N=6 | |
|---|---|---|---|---|---|---|
| Toxicity grade | 3 | 4 | 3 | 4 | 3 | 4 |
| Leukopenia | 1 | - | 1 | 1 | - | 2 |
| Neutropenia | 1 | - | - | 1 | 1 | 2 |
| Febrile neutropenia | - | - | 1 | - | 3 | - |
| Anemia | - | - | 2 | - | - | 1 |
| Thrombocytopenia | - | - | 1 | - | 1 | - |

One patient did not receive the treatment because of disease progression.

| Toxicity | Dose level 1 (S-1 40 mg/m²) N=3 | | Dose level 2 (S-1 60 mg/m²) N=7 | | Dose level 3 (S-1 80 mg/m²) N=6 | |
|---|---|---|---|---|---|---|
| Toxicity grade | 3 | 4 | 3 | 4 | 3 | 4 |
| Anorexia | - | - | 2 | - | 2 | - |
| Mucositis | 1 | - | 4 | - | 5 | 1 |
| Dysphagia | 1 | - | 5 | - | 5 | 1 |
| Infection | 1 | - | 5 | - | 1 | - |
| Dermatitis | - | - | 2 | - | 1 | - |
| Diarrhea | - | - | 1 | - | - | - |

| | N | No. of DLT | Event |
|---|---|---|---|
| Dose level 1 (S-1 40 mg/m²) N=3 | 3 | 0 | |
| Dose level 2 (S-1 60 mg/m²) N=7 | 7 | 2* | Febrile Neutropenia >4 days Grade 3 Diarrhea |
| Dose level 3 (S-1 80 mg/m²) N=6 | 6 | 2 | Febrile Neutropenia >4 days |

*One patient who had febrile neutropenia > 4 days turned out to have myelodysplastic syndrome (MDS)

| | Entry.No. | Response | Relapse | Salvage surgery |
|---|---|---|---|---|
| Dose level 1 (S-1 40 mg/m²) N=3 | 1 | PR (pCRª) | - | yes |
| | 3 | CR | Regional LN | no |
| | 4 | CR | - | - |
| Dose level 2 (S-1 60mg/m²) N=7 | 5 | CR | Primary→Lung | yes |
| | 6 | CR | - | - |
| | 7 | CR | - | - |
| | 14 | CR | - | - |
| | 15 | PRᵇ | - | - |
| | 16 | CR | Local | yes |
| | 17 | CR | - | - |
| Dose level 3 (S-1 80mg/m²) N=6 | 8 | PR (pCRª) | - | yes |
| | 9 | CR | Liver | no |
| | 10 | CR | - | - |
| | 11 | CR | - | - |
| | 12 | CR | Liver, Bone | no |
| | 13 | CR | - | - |

Response was evaluated according to RECIST criteria.
ªpCR: Pathological CR, ᵇPR has lasted more than 6 months
One patient (No. 2) did not receive the CRT because of disease progression.

Before            After

FIG. 9

METHOD FOR TREATING HEAD AND NECK CANCER

BACKGROUND OF THE INVENTION

1. Field of the Invention

The present invention relates to a method for the treatment of head and neck cancer.

2. Background Art

In the United States, 50,000 people are diagnosed with head and neck cancers per year, and about 60% of them fall into locally advanced stage III/IV cases. Head and neck tumors exhibit a variety of tissue types, and 80% or more of the cases are classified as squamous cell carcinomas. Therefore, treatment methods heretofore developed have focused primarily on squamous cell carcinomas. The head and neck section is an assembly of a plurality of organs, and the primary foci of head and neck cancer include the paranasal sinus, the epipharynx, the oropharynx, the oral cavity, the hypopharynx, the larynx, and the salivary glands. The prognosis of the head and neck cancer varies, depending on the primary focus thereof. Among head and neck cancers, the prognosis is the worst in hypopharynx cancer and the most favorable in epipharynx cancer. In particular, locally advanced head and neck cancer exhibits a poor prognosis, and a five-year survival rate is reported as 20 to 50%.

A variety of methods are available for the treatment of head and neck cancer, including surgical resection, radiotherapy, chemoradiotherapy, and chemotherapy, which are selected in accordance with the stage and affected site. Generally, when the cancer is resectable, surgical resection is used as a standard method. If the cancer is in an early stage, radiotherapy or a similar treatment is performed. Recently, there are many patients who want to maintain function of an organ such as the larynx and therefore, radiotherapy and chemotherapy have been used in combination in order to attain higher local controllability. When a patient desires to conserve the larynx, chemoradiotherapy is conceived to be a standard treatment, on the basis of randomized trial results comparing chemoradiotherapy with radiation therapy alone. Meanwhile, radiotherapy has conventionally been applied to locally advanced head and neck cancer, to which radical resection cannot be applied. However, the treatment results are unsatisfactory. Randomized trial results comparing chemoradiotherapy with radiation therapy alone show that chemoradiotherapy exhibits considerably higher local controllability and survival rate and thus is conceived to be a standard treatment for unresectable head and neck cancer, although potentiation of toxicity to the bone marrow and the digestive system (e.g., mucositis) is observed. Thus, regardless of whether the cancer is resectable, chemoradiotherapy is widely applied to locally advanced head and neck cancers (see Non-Patent Documents 1 to 9).

Heretofore, a variety of anti-cancer agents have been used in combination with radiotherapy. However, a standard regimen in terms of the anti-cancer agent to be combined, the dose and way of administration, administration schedule, etc. which is to be used with radiotherapy has not yet been established. From early 1980's, combination chemotherapies which generally use cisplatin (CDDP) have been developed in the U.S. and Europe, and the FP therapy (i.e., combination chemotherapy using 5-fluorouracil (5-FU) and cisplatin) has been reported to exhibit a high antitumor effect with a response rate of 88% and a CR rate of 19%, with respect to locally advanced head and neck cancer (Non-Patent Document 10). Since then, the FP therapy has been recognized to be the most effective regimen for locally advanced head and neck cancer, and has been widely used in combination with radiotherapy. In a meta-analysis carried out by Browman and others, regimens using platinum-based drugs such as cisplatin, Mitomycin C, 5-FU, and Bleomycin, respectively, exhibit odds ratios of 0.57 (95% CI, 0.46-0.71; p<0.00001), 0.54 (95% CI, 0.30-0.95; p=0.032), 0.66 (95% CI, 0.39-1.10; p=0.11), and 0.80 (95% CI, 0.50-1.29; p=0.36), indicating that the regimen using a platinum-based drugs exhibits the highest add-on effect on survival (see Non-Patent Document 9). Furthermore, although use of an anti-cancer agent alone and combination chemotherapy exhibit odds ratios of 0.63 (95% CI, 0.48-0.81; p=0.0004) and 0.63 (95% CI, 0.48-0.83, p=0.0009), respectively, which are equal to each other, the FP therapy exhibits an odds ratio of 0.53 (95% CI, 0.41-0.69; p<0.00001), indicating that this therapy promises the highest add-on effect on survival. As described hereinabove, a platinum-based drug such as cisplatin has been recognized as a key drug to locally advanced head and neck cancer, and for this, cisplatine alone or the FP therapy is widely used.

Use of S-1 alone (80 mg/m$^2$/day, four-week administration, followed by two-week rest) exhibits response rate of 34.1% (29/85) with respect to advanced/relapsed head and neck cancer, and a percent efficacy of 30.4% (21/69) with respect to the relapse cases in which treatment using radiotherapy, combination chemotherapy (e.g., a platinum-based drug and a 5-FU-based anti-malignant-tumor agent), etc. has already been performed. The response rate is higher than 15%, which is the response rate obtained through use of a 5-FU drug alone (continuous intravenous infusion) (see Non-Patent Documents 11). A combination chemotherapy (S-1 and cisplatin) has been extensively used with advanced/relapsed gastric cancer (see, for example, Non-Patent Documents 12 and 13), and some cases of applying such a therapy to head and neck cancer have also been reported recently (see, for example, Non-Patent Document 14 to 20). For example, Fujii and others carried out a phase I/II trial of an S-1+CDDP therapy with respect to relapsed/advanced head and neck cancer. In the trial, 38 patients in total were tested, and excellent antitumor effect was attained with a best response of 67.6% (23/34) and a confirmed response of 44.1% (15/34). In this trial, toxicities of grade 3 or higher were found to be expressed as follows: neutropenia 11.8%, anemia 8.8%, thrombocytopenia 11.8%, anorexia 26.5%, nausea 14.7%, fatigue 8.8%, and diarrhea 2.9% (see Non-Patent Document 20).

Non-Patent Document 1:
Marcial V A, Pajak T F. Radiation therapy alone or in combination with surgery in head and neck cancer. *Cancer* 1985; 55(9 Suppl): 2259-65.

Non-Patent Document 2:
Adelstein D J, Li Y, Adams G L, et al. An intergroup phase III comparison of standard radiation therapy and two schedules of concurrent chemoradiotherapy in patients with unresectable squamous cell head and neck cancer. *J Clin Oncol* 2003; 21(1): 92-8.

Non-Patent Document 3:
Brizel D M, Albers M E, Fisher S R, et al. Hyperfractionated irradiation with or without concurrent chemotherapy for locally advanced head and neck cancer. *N Engl J Med* 1998; 338(25): 1798-804.

Non-Patent Document 4:
Merlano M, Benasso M, Corvo R, et al. Five-year update of a randomized trial of alternating radiotherapy and chemotherapy compared with radiotherapy alone in treatment of unresectable squamous cell carcinoma of the head and neck. *J Natl Cancer Inst* 1996; 88(9): 583-9.

Non-Patent Document 5:
20. Zakotnik B, Smid L, Budihna M, et al. Concomitant radiotherapy with mitomycin C and bleomycin compared with radiotherapy alone in inoperable head and neck cancer: final report. *Int J Radiat Oncol Biol Phys* 1998; 41(5): 1121-7.

Non-Patent Document 6:
Adelstein D J, Lavertu P, Saxton J P, et al. Mature results of a phase III randomized trial comparing concurrent chemoradiotherapy with radiation therapy alone in patients with stage III and IV squamous cell carcinoma of the head and neck. *Cancer* 2000; 88(4): 876-83.

Non-Patent Document 7:
Wendt T G, Grabenbauer G G, Rodel C M, et al. Simultaneous radiochemotherapy versus radiotherapy alone in advanced head and neck cancer: a randomized multicenter study. *J Clin Oncol* 1998; 16(4): 1318-24.

Non-Patent Document 8:
Pignon J P, Bourhis J, Domenge C, Designe L. Chemotherapy added to locoregional treatment for head and neck squamous-cell carcinoma: three meta-analyses of updated individual data. MACH-NC Collaborative Group. Meta-Analysis of Chemotherapy on Head and Neck Cancer. *Lancet* 2000; 355(9208): 949-55.

Non-Patent Document 9:
Browman G P, Hodson D I, Mackenzie R J, Bestic N, Zuraw L. Choosing a concomitant chemotherapy and radiotherapy regimen for squamous cell head and neck cancer: A systematic review of the published literature with subgroup analysis. *Head Neck* 2001; 23(7): 579-89.

Non-Patent Document 10:
Kish J, Drelichman A, Jacobs J, et al. Clinical trial of cisplatin and 5-FU infusion as initial treatment for advanced squamous cell carcinoma of the head and neck. *Cancer Treat Rep* 1982; 66(3): 471-4.

Non-Patent Document 11:
Inuyama Y, Kida A, Tsukuda M, Kohno N, Satake B. [Late phase II study of S-1 in patients with advanced head and neck cancer]. *Gan To Kagaku Ryoho* 2001; 28(10): 1381-90.

Non-Patent Document 12:
Takahashi T, Saikawa Y, et al. Histological Complete Response in a Case of Advanced Gastric Cancer Treated by Chemotherapy with S-1 Plus Low-dose Cisplatin and Radiation. *Jpn. J. Clin. Oncol.,* 2003; 33(11); 584-588

Non-Patent Document 13:
Iwase H, Indo T, et al. Esophageal cancer with colonic metastasis successfully treated by chemoradiotherapy followed by chemotherapy with S-1 and cisplatin. *Int. J. Clin. Oncol.,* 2004; 9; 394-402

Non-Patent Document 14:
Japanese Journal of Cancer and Chemotherapy, 30(12), p1945-1947, 2003.11

Non-Patent Document 15:
Japanese Journal of Cancer and Chemotherapy, 30(4), p511-515, 2003.4

Non-Patent Document 16:
Japanese Journal of Cancer and Chemotherapy, 30(9), p1309-1312, 2003.9

Non-Patent Document 17:
Japanese Journal of Cancer and Chemotherapy, 31(2), p215-217, 2004.2

Non-Patent Document 18:
Head and Neck Cancer, 30(2), p282(2004).

Non-Patent Document 19:
Harada K, Kawaguchi S, Supriatno, Onoue T, Yoshida H, Sato M. Combined effects of the oral fluoropyrimidine anticancer agent, S-1 and radiation on human oral cancer cells. *Oral Oncol* 2004; 40(7): 713-9.

Non-Patent Document 20:
M. Fujii, S. Endo, et al., A Phase I/II study of S-1 plus Cisplatin (CDDP) in Patients with Head and Neck Cancer (HNC). *Proc. ASCO* 24: 513 (abstr 5552), 2005.

However, even when the aforementioned anti-cancer drugs are used in combination or concurrently with radiotherapy, the treatment efficacy to advanced head and neck cancer is unsatisfactory. Thus, demand has arisen for a new treatment method. Furthermore, it is generally very difficult to predict whether or not a treatment method which has been effective for a certain cancer type is also effective with respect to other types of cancer. Therefore, the timing of combination of radiotherapy with chemotherapy and selection of the type of chemotherapy are determined only on the basis of actual clinical data.

SUMMARY OF THE INVENTION

The present inventor has found that, when radiotherapy and administration, in combination, of the aforementioned S-1 (a drug containing Tegafur, Gimeracil, and Oteracil potassium) and cisplatin are performed according to a specific schedule, the advanced head and neck cancer is significantly shrunk. The present invention has been accomplished on the basis of this finding.

Accordingly, the present invention provides a method for the treatment of advanced head and neck cancer, wherein the method comprising administering, in combination, S-1 and cisplatin and performing radiation according to the following schedule:

(1) performing radiation at a dose of 1.8 to 2 Gy/day for five days per week for 33 to 35 times (7 weeks), (2) administering S-1 at a dose of 40 to 80 mg/m$^2$/day (as Tegafur dose) every day during a period of day 1 of treatment to day 14 and every day during a period of day 36 to day 49, and (3) administering, through intravenous injection, cisplatin at a dose of 10 to 20 mg/m$^2$/day for 3 to 8 continuous days during a period of day 1 of treatment to day 14 and for 3 to 8 continuous days during a period of day 36 to day 49.

DETAILED DESCRIPTION OF PREFERRED EMBODIMENTS

The method for the treatment of the present invention comprises performing radiation and administering, in combination, S-1 and cisplatin, according to a specific schedule.

As used herein, the drug "S-1" is a peroral anti-malignant-tumor drug that contains Tegafur, Gimeracil, and Oteracil potassium in a molar ratio of 1:0.4:1. Tegafur, which is 1-(2-tetrahydrofuryl)-5-fluorouracil, is a prodrug for 5-FU. Gimeracil is a decomposition-inhibitor for 5-FU, and Oteracil potassium is a phosphating-inhibitor for 5-FU (Shirasaka T, Shimamoto Y, Ohshimo H, et al: Development of a novel form of an oral 5-fluorouracil derivative (S-1) directed to the potentiation of the tumor selective cytotoxicity of 5-fluorouracil by two biochemical modulators. Anti-Cancer Drugs 7: 548-557, 1996.).

The dose of S-1 is preferably, from the viewpoint of efficacy and side-effect prevention, 40 to 80 mg/m$^2$/day (as Tagafur dose), particularly preferably 60 mg/m$^2$/day. S-1 is administered once to several times per day, preferably twice per day in a divided manner at the above dose. From the viewpoint of enhancement of treatment efficacy and prevention of side effects, S-1 is preferably administered every day during a period of day 1 of treatment to day 14 and every day during a period of day 36 to day 49, in consideration of the schedule of radiation.

Cisplatin (CDDP) is a platinum-based anti-tumor agent. Preferably, cisplatin is administered at a dose of 10 to 20 mg/m$^2$/day, particularly preferably 20 mg/m$^2$/day. Cisplatin is preferably administered, through intravenous injection, for 3 to 8 continuous days (particularly 4 continuous days) during a period of day 1 of treatment to day 14, and for 3 to 8 continuous days (particularly 4 continuous days) during a period of day 36 to day 49, more preferably for 4 continuous days during a period of day 4 to day 14 and for 4 continuous days during a period of day 39 to day 49 through intravenous injection, particularly preferably for 4 continuous days during a period of day 8 to day 11 and for 4 continuous days during a period of day 43 to day 46 through intravenous injection, in consideration of the schedule of radiation. Note that, preferably, cisplatin is administered through intravenous injection over about 30 minutes to about 2 hours, followed by sufficient hydration.

The total dose of cisplatin during the aforementioned continuous administration period is preferably 120 to 200 mg/m$^2$, particularly preferably 160 mg/m$^2$. One characteristic feature of the treatment method of the invention is that the total dose is divided into 10 to 20 mg/m$^2$/day and continuous administration is carried out according to a specific schedule. For example, in the case where the daily dose is 20 mg/m$^2$/day, cisplatin is administered for 4 continuous days during a period of day 8 to day 11, and for 4 continuous days during a period of day 43 to day 46 through intravenous injection, whereas in the case where the daily dose is 10 mg/m$^2$/day, cisplatin is administered for 8 continuous days during a period of day 4 to day 11 and for 8 continuous days during a period of day 39 to day 46 through intravenous injection.

The dose of S-1 with respect to a patient is determined in accordance with body surface area (BSA) calculated from the height and body weight of the patient. The body surface area is calculated appropriately through a known method depending on the race, sex, health conditions, symptom, etc., of the patient. For example, the following formulas 1 to 5 may be employed. When the patient is a Mongoloid (including Japanese), the following formula 6 is preferably employed, whereas when the patient is a non-Mongoloid (including Caucasian), the following formula 2(b) is preferably employed.

1. The Mosteller formula (see N Engl J Med 1987 Oct. 22; 317(17): 1098 (letter)):

$$BSA\ (m^2) = ([height\ (cm) \times body\ weight\ (kg)]/3600)^{1/2}$$

2. The Du Bois and Du Bois formula (see Arch Int Med 1916 17: 863-71; J Clin Anesth. 1992; 4(1): 4-10):

$$BSA\ (m^2) = 0.20247 \times height^{0.725}\ (m) \times body\ weight^{0.425}\ (kg) \quad (a)$$

$$BSA\ (m^2) = 0.007184 \times height^{0.725}\ (cm) \times body\ weight^{0.425}\ (kg) \quad (b)$$

3. The Haycock formula (see The Journal of Pediatrics 1978 93:1: 62-66)

$$BSA\ (m^2) = 0.024265 \times height^{0.3964}\ (cm) \times body\ weight^{0.5378}\ (kg)$$

4. The Gehan and George formula (see Cancer Chemother Rep 1970 54: 225-35)

$$BSA\ (m^2) = 0.0235 \times height^{0.42246}\ (cm) \times body\ weight^{0.51456}\ (kg)$$

5. The Boyd formula (see Minneapolis: University of Minnesota Press, 1935)

$$BSA\ (m^2) = 0.0003207 \times height^{0.3}\ (cm) \times body\ weight^{(0.7285-(0.0188 \times LOG(grams)))}\ (grams)$$

6. Fujimoto et al. (see Nihon Eisei Gakkai Shi, 23(5), 443-450, 1968)

$$BSA\ (m^2) = 88.83 \times height^{0.663}\ (cm) \times body\ weight^{0.444}\ (kg)$$

For example, body surface area of a cancer patient (height: 170 cm, body weight: 65 kg) is calculated as 1.707 (m$^2$) by formula 6 above (i.e., $88.83 \times 170^{0.663}$ (cm) $\times 65^{0.444}$ (kg)). When the dose per BSA for the patient is predetermined to be 60 mg/m$^2$/day, the daily dose is calculated to be about 102 mg (1.707×60). Thus, the daily dose of S-1 is predetermined to be 100 mg.

The dose of CDDP with respect to a patient is also determined in accordance with body surface area (BSA) calculated from the height and body weight of the patient. The body surface area is calculated appropriately through a known method depending on the race, sex, health conditions, symptom, etc., of the patient. For example, the formula 2(b) above may be employed. For example, body surface area of a cancer patient (height: 170 cm, body weight 65 kg) is calculated by formula 2(b) above, the body surface area is calculated as about 1.754 (m$^2$) (i.e., $0.007184 \times 170^{0.725}$ (cm) $\times 65^{0.425}$ (kg)). When the dose per BSA for the patient is predetermined to be 20 mg/m$^2$/day, the daily dose is calculated to be about 35 mg (1.754×20). Thus, the daily dose of CDDP is predetermined to be 35 mg.

S-1 is a capsule formulation for peroral administration and available as "TS-1 capsule" on the market. No particular limitation is imposed on the drug form of S-1, so long as the form allows peroral administration. Examples of the drug form include tablets, coated tablets, pills, powder, granules, liquid, suspension, and emulsion. These drug formulations may be produced through a drug preparation method generally known in the art by use of a pharmaceutically acceptable carrier or other additives.

Examples of the carrier employed for forming the tablets include vehicles such as lactose, sucrose, sodium chloride, glucose, urea, starch, calcium carbonate, kaolin, crystalline cellulose, and silicic acid; binders such as water, ethanol, propanol, cornstarch, simple syrup, glucose liquid, starch liquid, gelatin solution, carboxymethylcellulose, shellac, methylcellulose, hydroxypropylcellulose, hydroxypropylmethylcellulose, potassium phosphate, and polyvinylpyrrolidone; disintegrants such as dry starch, sodium alginate, agar powder, laminaran powder, sodium hydrogencarbonate, calcium carbonate, polyoxyethylene sorbitan fatty acid esters, sodium lauryl sulfate, stearic acid monoglyceride, starch, and lactose; disintegration inhibitors such as sucrose, stearic acid, cacao butter, and hydrogenated oil; absorption promoters such as quaternary ammonium bases and sodium lauryl sulfate; moisturizing agents such as glycerin and starch; adsorbents such as starch, lactose, kaolin, bentonite, and colloidal silicic acid, and lubricants such as purified talc, stearic acid salts, boric acid powder, and polyethylene glycol. In accordance with needs, the tablets may further be modified to form coated tablets having a generally employed coating; e.g., sugar-coated tablets, gelatin-coated tablets, enteric tablets, film-coated tablets, double-layered tablets, and multi-layered tablets.

In preparation of pills, carriers to be employed include, for example, vehicles such as glucose, lactose, starch, cacao butter, hydrogenated vegetable oil, kaolin, and talc; binders such as acacia powder, tragacanth powder, gelatin, ethanol; and disintegrants such as laminaran and agar.

Peroral liquid drugs may be produced through a routine method by use of a sweetener, a buffer, a stabilizer, a flavoring agent, or a similar additive, whereby peroral liquid drugs, syrups, elixirs, etc. can be provided. Examples of the sweetening agent include sucrose, bitter orange peel, citric acid, and tartaric acid. Examples of the buffer include sodium citrate, and examples of the stabilizer include tragacanth, acacia, and gelatin.

The aforementioned drugs may further contain, in accordance with needs, a colorant, a preservative, a perfume, a flavoring agent, a sweetening agent, and other pharmaceutical drugs.

Since in many cases head and neck cancer patients suffer passage disorders, administration of a capsule-form drug may raise difficulty in swallowing. Thus, in the combination therapy of the present invention, one preferred embodiment is administration through feeding tubes of S-1. No particular limitation is imposed on the method of administration through feeding tubes, so long as it is a generally known method. For example, administration through feeding tubes may be carried out in accordance with the method disclosed in Jpn. J. Pharm. Health Care Sci., 27(5), 461-472 (2001). In one method, the content of TS-1 capsules is suspended in water or an enteral nutritional liquid, and the suspension is administered through a catheter. In an alternative method, a capsule formulation is broken in an injector without removal of the capsule, and the suspension obtained in the injector is administered by means of a catheter (disintegration-suspension method). The administration through feeding tubes may be carried out by means of, for example, a nasotracheal or gastrostomy catheter.

Cisptatin is preferably administered in the form of intravenous injection.

Radiation is preferably performed five days per week at a dose of 1.8 to 2 Gy/day (particularly preferably 2.0 Gy/day) for 33 to 35 times (particularly preferably 35 times (7 weeks)). The total dose of radiation is preferably 66 to 70 Gy, particularly preferably 70 Gy. The radiotherapy to be used in the present invention may be performed through a protocol which is generally used in the art and know to the those skilled in the art. For example, the radiotherapy includes cesium, iridium, iodine, and cobalt radiation. The radiotherapy is preferably focused locally on the tumor site(s) and tissue. A typical radiotherapy is performed for 2 to 3 minutes a day at the aforementioned dose for 33 to 35 times (7 weeks).

One preferred embodiment of the method of the present invention for the treatment of advanced head and neck cancer comprises (1) performing radiation at a dose of 2.0 Gy/day for five days per week for 33 to 35 times (7 weeks), (2) administering S-1 at a dose of 40 to 80 mg/m$^2$/day (as Tegafur dose) every day during a period of day 1 of treatment to day 14 and every day during a period of day 36 to day 49, and (3) administering, through intravenous injection, cisplatin at a dose of 20 mg/m$^2$/day for 4 continuous days during a period of day 1 of treatment to day 14 and for 4 continuous days during a period of day 36 to day 49.

One more preferred embodiment of the method of the present invention for the treatment of advanced head and neck cancer comprises (1) performing radiation at a dose of 2.0 Gy/day for five days per week for 35 times (7 weeks), (2) administering S-1 at a dose of 60 mg/m$^2$/day (as Tegafur dose) every day during a period of day 1 of treatment to day 14 and every day during a period of day 36 to day 49, and (3) administering, through intravenous injection, cisplatin at a dose of 20 mg/m$^2$/day for 4 continuous days during a period of day 8 of treatment to day 11 and for 4 continuous days during a period of day 43 to day 46.

The patient to which the method of the present invention is applied is a patient suffering advanced head and neck cancer, preferably a patient suffering locally advanced head and neck cancer, more preferably a patient suffering unresectable locally advanced head and neck cancer which has heretofore been treated with only insufficient effects, particularly preferably a patient diagnosed with head and neck cancer classified as N2c or N3 by the TNM classification (see UICC TNM Classification of Malignant Tumors sixth edition). The classification code "N2c" means a metastasis in bilateral or contralateral lymph nodes, ≦6 cm in greatest dimension, whereas the classification code "N3" means a degree of lymph nodal metastasis in which a lymph node >6 cm in greatest dimension. The treatment method of the present invention is preferably applied to a patient suffering advanced head and neck cancer, who has undergone no treatment. However, needless to say, the method may also be applied to a head and neck cancer patient having a local cancer site that has relapsed after operation.

EXAMPLE

The present invention is further described in detail by the following examples; however, it should not be construed that the present invention is limited thereto.

Example 1

The effect of treatment of head and neck cancer by combination of radiotherapy and chemotherapy in which S-1 and cisplatin (CDDP) are used in combination is examined.

(1) Experimental Method

Patients enrolled into this study had histologically or cytologically confirmed squamous cell carcinoma of head and neck, unresectable locally advanced cancer and had received no prior chemotherapy or radiotherapy.

Unresectable locally advanced caner was defined as technical unresectability or physician's decision based on low chance of surgical curability, including N2c or N3, which mean a metastasis in bilateral or contralateral lymph nodes, ≦6 cm in greatest dimension, or a degree of lymph nodal metastasis in which a lymph node is >6 cm in greatest dimension.

(2) Treatment Schedule

Figure 1:
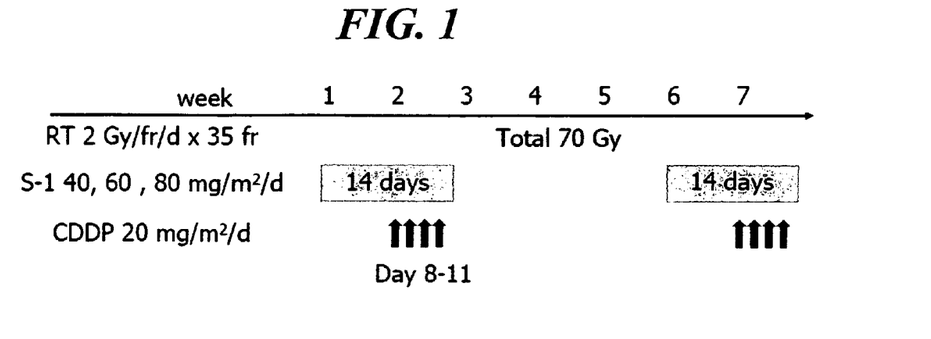
FIG. 1 shows a schedule of administration (RT: radiotherapy, CDDP: cisplatin)

Chemoradiotherapy consisted of two cycles of administration of S-1 twice daily on day 1 to day 14 at escalating doses (40, 60, 80 mg/m$^2$/day), and infusion of cisplatin over 2 hours at 20 mg/m$^2$/day on days 8 to 11, repeated every 5 weeks with concurrent radiotherapy of 70 Gy in 35 fractions. Specifically, 35 fractions of radiation was performed in a period of 7 weeks at a dose of 2 Gy/day; S-1 was administered at a dose of 40, 60, 80 mg/m$^2$/day for every day during each period from day 1 to day 14 and from day 36 to day 49 in the treatment schedule; and cisplatin was administered intravenously 4 continuous days at a dose of 20 mg/m$^2$/day during a period of day 8 to day 11 and a period of day 43 to day 46 (refer to FIG. 1). Further, two additional cycles of S-1 and cisplatin administration were planned for the patients exhibiting effect of treatment (i.e., those who exhibiting CR or PR) after completion of chemoradiotherapy.

In this trial, S-1 was administered through feeding tubes by means of nasotracheal or gastrostomy catheter to 6 of the patients who were subjected to the treatment due to disturbed passage.

(3) Definition of DLT and MTD

Figure 2:
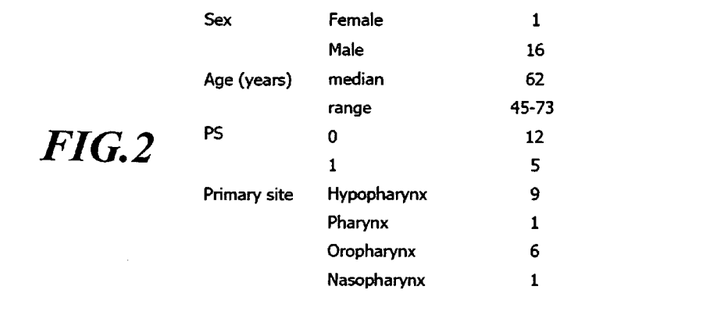
FIG. 2 is a table showing characteristics of patients.

DLT was defined according to National Cancer Institute Common Toxicity Criteria ver.2.0 when one or more of the following adverse events was observed within 30 days of completion of concurrent chemoradiotherapy.
a) Febrile Neutropenia lasting more than 4 days
b) Grade 4 Thrombocytopenia (<10,000/mm$^3$)
c) Grade 4 vomiting
d) Grade 3 and 4 non-hematological toxicity except grade 3 anorexia, nausea, vomiting, stomatitis, esophagitis and infection due to stomatitis
e) Treatment off due to adverse event
f) Treatment-related death (4) Patients, Classification and the Result Patients, classification and the result are shown in FIG. 2. Only one patient was female. Median age was 62. The majority of primary sites were either hypopharynx or oropharynx.

(5) Stage Distribution

Figure 3:
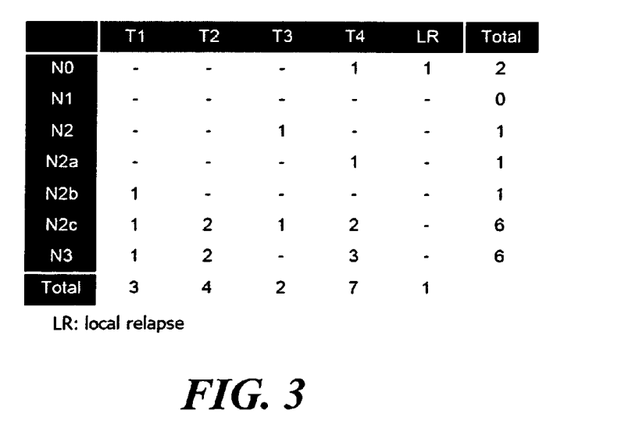
FIG. 3 is a table showing tumor stage distribution.

As shown in FIG. 3, patients were classified according to TNM Classification of Malignant Tumors. Most patients were diagnosed as N2c and N3.

(6) Toxicity and Dose-limiting Toxicity

Figure 4:
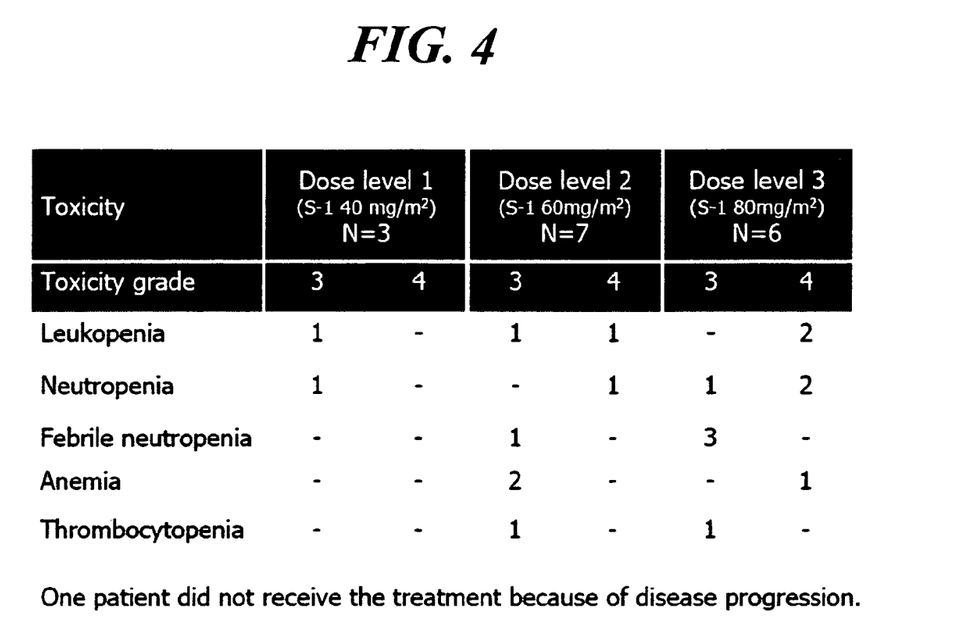
FIG. 4 is a table showing grade 3 and 4 hematological toxicities.

The hematological toxicities of grade 3 and 4 are shown in FIG. 4. The most common hematological toxicity is neutropenia. The incidence and severity of neutropenia was dose-dependent.

Figure 5:
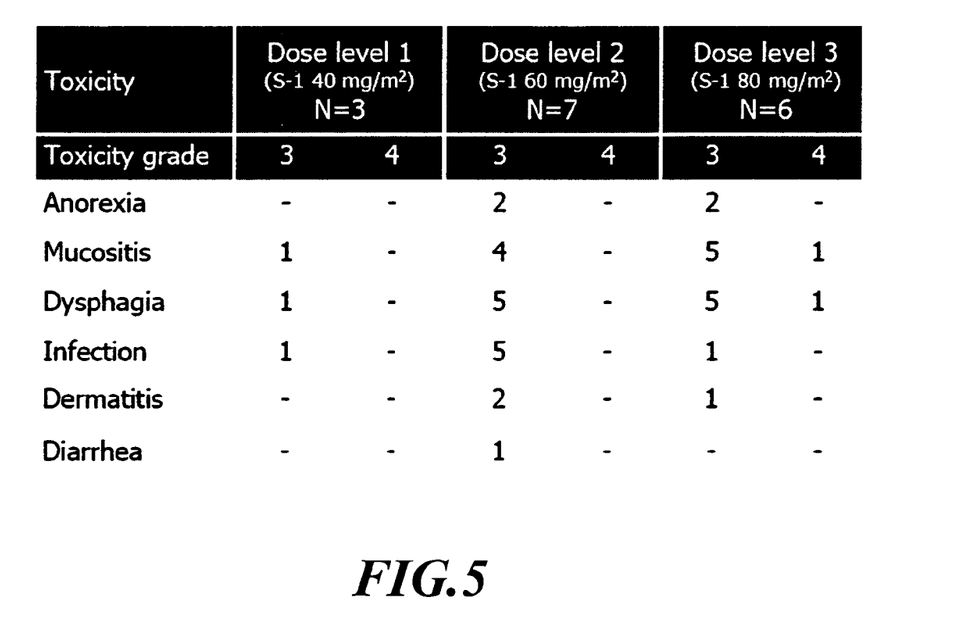
FIG. 5 is a table showing grade 3 and 4 non-hematological toxicities.

The non-hematological toxicities of grade 3 and 4 are shown in FIG. 5. Most common toxicities were mucositis and dysphasia and infection due to mucositis. The incidence and severity of mucositis and dysphasia was also dose-dependent. All patients treated at the dose level 3 (i.e., S-1:80 mg/m$^2$/day) experienced with grade 3 or 4 mucositis and dysphasia.

Figure 6:
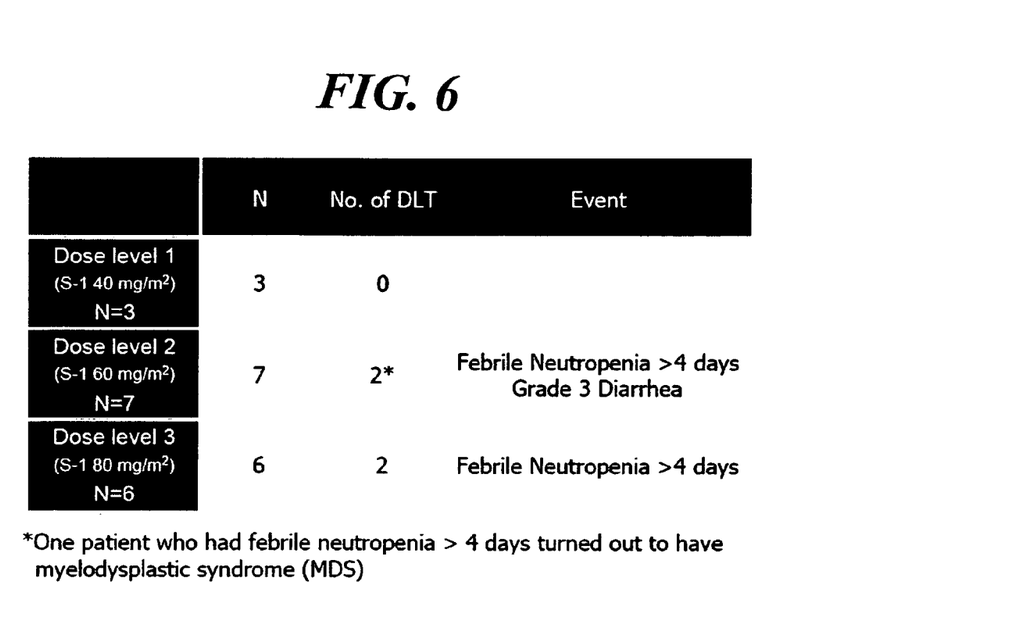
FIG. 6 is a table showing dose-limiting toxicities (DLT)

Dose-Limiting Toxicities (DLT) are shown in FIG. 6. At dose level 1 (i.e., S-1:40 mg/m$^2$/day), initial 3 patients exhibited a minor hematological toxicity, at which level dose-limiting toxicity was not recognized. At dose level 2 (i.e., S-1:60 mg/m$^2$/day), 2 out of 7 exhibited dose-limiting toxicity; however, the amount of administration of S-1 continued on to dose level 3 (i.e., S-1:80 mg/m$^2$/day) in accordance with the prescript of dose-increase. At this level, 2 out of 6 developed febrile neutropena lasting more than 4 days. From these results, it was suggested that the maximum tolerated dose (MTD) of S-1 was 80 mg/m$^2$/day.

From above results, it was suggested that the recommended dose of S-1 in combination with cisplatin and radiotherapy is 60 mg/m$^2$/day.

(7) Efficacy of Treatment

Figure 7:
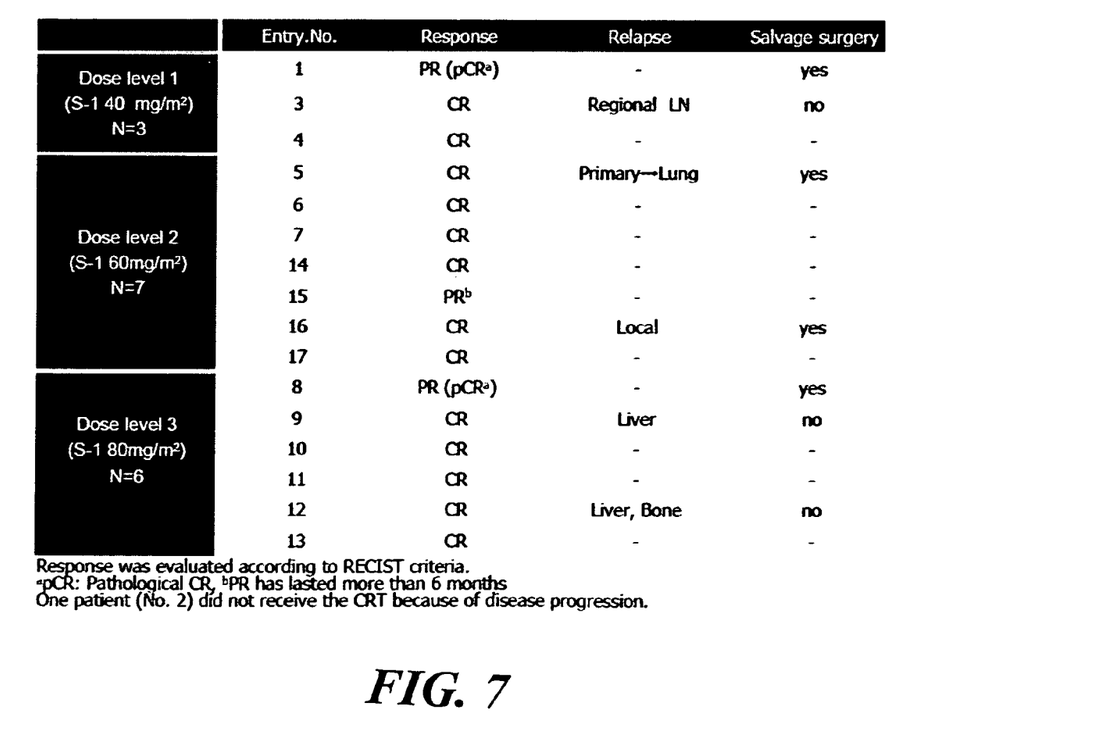
FIG. 7 is a table showing efficacy (n=16)
Figure 9:
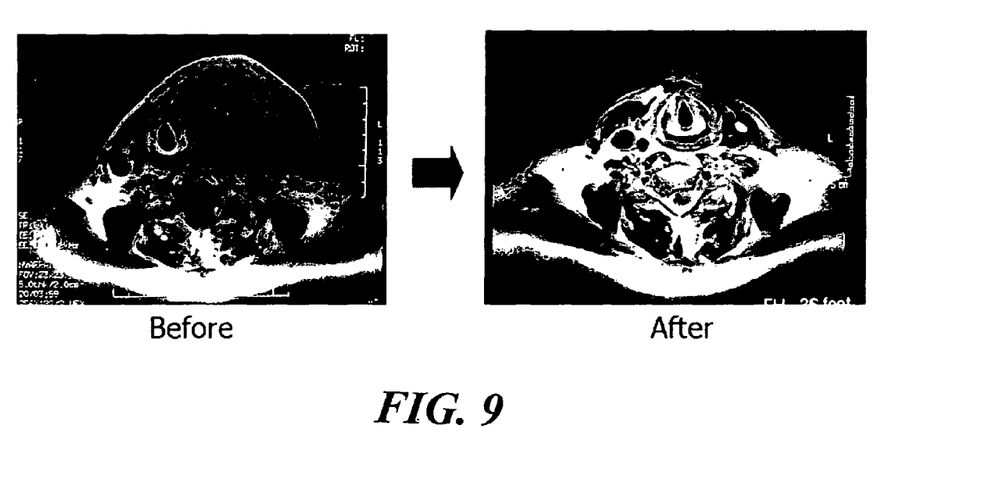
FIG. 9 shows photographs of a hypopharynx cancer image of a T1N3M0 patient.

The efficacy of treatment is shown in FIG. 7. 16 out of 17 patients treated with the chemoradiotherapy were assessable for response. 13 patients (81%) had a complete response (CR: a state in which all detectable tumor has disappeared for more than 4 weeks) according to RECIST, which is the evaluation criteria for effect of cancer pharmacologic therapy (refer to Journal of the National Cancer Institute 92(3):205-16, 2000). Further, 2 patients, who were found to have a residual neck lymph node metastasis, underwent salvage neck dissection and their complete response was pathologically confirmed (refer to FIG. 9). In addition, partial response (PR: a state in which shrinkage of approximately more than 50% of the tumor is maintained for more than 4 weeks) was confirmed with one patient.

Figure 8:
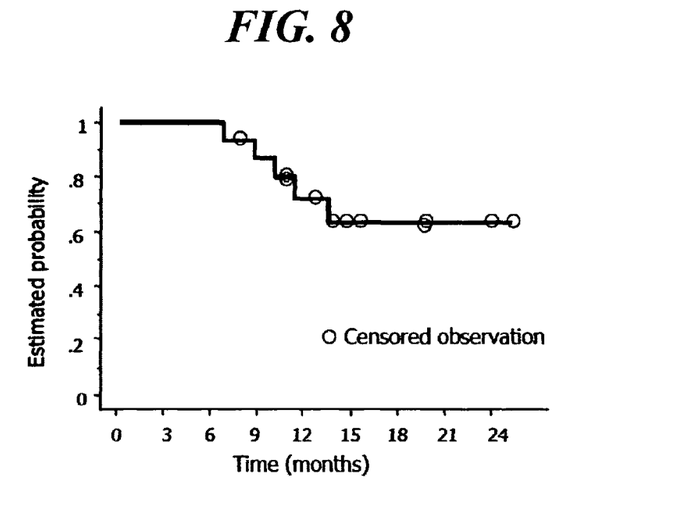
FIG. 8 is a graph showing progression-free survival (n=16)

Further, as shown in FIG. 8, at a median follow up time of 14.3 months, all the patients who were treated with the regimen described herein were alive and 1-yr progression-free survival rate was 72.3%.

What is claimed is:

1. A method for treating advanced head and neck cancer comprising:
   performing radiation 33-35 times at a dose of 1.8-2.0 Gy/day for five days per week;
   administering S-1 at a Tegafur dose of 40-80 mg/m$^2$/day every day during a period of day 1-14 of treatment and every day during a period of day 36-49 of treatment; and
   administering cisplatin at a dose of 10-20 mg/m$^2$/day for 3-8 continuous days during a period of day 1-14 of treatment and for 3-8 continuous days during a period of day 36-49 of treatment.

2. The method for treating advanced head and neck cancer according to claim 1, wherein radiation is performed at a dose of 2.0 Gy/day.

3. The method for treating advanced head and neck cancer according to claim 1, wherein the total dose of radiation is 66-70 Gy.

4. The method for treating advanced head and neck cancer according to claim 1, wherein the total dose of radiation is 70 Gy.

5. The method for treating advanced head and neck cancer according to claim 1, wherein radiation is selected from cesium, iridium, iodine, and cobalt radiation.

6. The method for treating advanced head and neck cancer according to claim 1, wherein S-1 is administered orally.

7. The method for treating advanced head and neck cancer according to claim 1, wherein S-1 is administered orally either once per day, or in two to several divided doses per day.

8. The method for treating advanced head and neck cancer according to claim 1, wherein S-1 comprises Tegafur, Gimeracil, and Oteracil potassium in a molar ratio of 1:0.4:1.

9. The method for treating advanced head and neck cancer according to claim 1, wherein S-1 is administered at a Tegafur dose of 60 mg/m$^2$/day every day during a period of day 1-14 of treatment and every day during a period of day 36-49 of treatment.

10. The method for treating advanced head and neck cancer according to claim 1, wherein cisplatin is administered intravenously.

11. The method for treating advanced head and neck cancer according to claim 1, wherein cisplatin is administered intravenously during a period of about 30-120 minutes.

12. The method for treating advanced head and neck cancer according to claim 1, wherein cisplatin is administered at a dose of 20 mg/m$^2$/day.

13. The method for treating advanced head and neck cancer according to claim 1, wherein cisplatin is administered for 4 continuous days during a period of day 4-14 of treatment and for 4 continuous days during a period of day 39-49 of treatment.

14. The method for treating advanced head and neck cancer according to claim 1, wherein cisplatin is administered for 4 continuous days during a period of day 8-11 of treatment and for 4 continuous days during a period of day 43-46 of treatment.

15. The method for treating advanced head and neck cancer according to claim 1, wherein cisplatin is administered at a dose of 10 mg/m²/day.

16. The method for treating advanced head and neck cancer according to claim 1, wherein cisplatin is administered for 8 continuous days during a period of day 4-11 of treatment and for 8 continuous days during a period of day 39-46 of treatment.

17. The method for treating advanced head and neck cancer according to claim 1, wherein the total dose of cisplatin is 120-200 mg/m².

18. The method for treating advanced head and neck cancer according to claim 1, wherein the total dose of cisplatin is 160 mg/m².

19. The method for treating advanced head and neck cancer according to claim 1, wherein:
    radiation is performed 33-35 times at a dose of 2.0 Gy/day for five days per week;
    S-1 is administered at a Tegafur dose of 40-80 mg/m²/day every day during a period of day 1-14 of treatment and every day during a period of day 36-49 of treatment; and
    cisplatin is administered at a dose of 20 mg/m²/day for 4 continuous days during a period of day 1-14 of treatment and for 4 continuous days during a period of day 36-49 of treatment.

20. The method for treating advanced head and neck cancer according to claim 1, wherein:
    radiation is performed 35 times at a dose of 2.0 Gy/day for five days per week;
    S-1 is administered at a Tegafur dose of 60 mg/m²/day every day during a period of day 1-14 of treatment and every day during a period of day 36-49 of treatment; and
    cisplatin is administered at a dose of 20 mg/m²/day for 4 continuous days during a period of day 8-11 of treatment and for 4 continuous days during a period of day 43-46 of treatment.

21. The method for treating advanced head and neck cancer according to claim 1, wherein the method is applied to a patient suffering from locally advanced head and neck cancer.

22. The method for treating advanced head and neck cancer according to claim 1, wherein the method is applied to a patient suffering from unresectable locally advanced head and neck cancer.

23. The method for treating advanced head and neck cancer according to claim 1, wherein the method is applied to a patient diagnosed with head and neck cancer classified as N2c or N3 according to the International Union Against Cancer (UICC) TNM Classification of Malignant Tumors.

* * * * *